United States Patent
Jayaraman

(10) Patent No.: US 7,390,293 B2
(45) Date of Patent: Jun. 24, 2008

(54) MODIFICATION OF PROPERTIES AND GEOMETRY OF HEART TISSUE TO INFLUENCE FUNCTION

(76) Inventor: Swaminathan Jayaraman, 459 Lowell Pl., Fremont, CA (US) 94536

( * ) Notice: Subject to any disclaimer, the term of this patent is extended or adjusted under 35 U.S.C. 154(b) by 790 days.

(21) Appl. No.: 10/770,266

(22) Filed: Feb. 2, 2004

(65) Prior Publication Data
US 2004/0158123 A1 Aug. 12, 2004

Related U.S. Application Data

(63) Continuation of application No. 09/988,293, filed on Nov. 19, 2001, now Pat. No. 6,685,627, which is a continuation-in-part of application No. 09/414,708, filed on Oct. 8, 1999, now Pat. No. 6,360,749.

(60) Provisional application No. 60/103,824, filed on Oct. 9, 1998.

(51) Int. Cl.
*A61F 2/00* (2006.01)
(52) U.S. Cl. .......................................... 600/37
(58) Field of Classification Search .............. 600/37, 600/16–18; 128/897, 898; 606/139, 144, 606/148
See application file for complete search history.

(56) References Cited

U.S. PATENT DOCUMENTS

| | | | |
|---|---|---|---|
| 4,468,177 A | 8/1984 | Strimling | |
| 4,902,291 A | 2/1990 | Kolff | |
| 5,258,028 A | 11/1993 | Ersek | |
| 5,282,849 A | 2/1994 | Kolff | |
| 5,336,263 A | 8/1994 | Ersek | |
| 5,383,840 A | 1/1995 | Heilman | |
| 5,702,343 A | 12/1997 | Alferness | |

(Continued)

FOREIGN PATENT DOCUMENTS

WO  WO 97/13471  4/1997

(Continued)

OTHER PUBLICATIONS

Pelka, Wendy A., et al. "Reversible Hydrogels form Self-Assembling Articial Protein" Science, vol. 281., Jul. 17, 1998., p. 389-392.

(Continued)

*Primary Examiner*—Samuel G Gilbert
(74) *Attorney, Agent, or Firm*—Fleit Kain Gibbons Gutman Bongini & Bianco; Paul D. Bianco; Martin Fleit

(57) ABSTRACT

Materials, devices and methods for the treatment of congestive heart failure are disclosed. In these methods, the volume of the left ventricle is reduced, thereby increasing the efficiency of the pumping action of the heart. Volume reduction is accomplished by introduction of biocompatible materials into the wall of the left ventricle, or into the ventricle itself. Also disclosed is a method for ventricular geometry reduction wherein flexible, elastic bands are attached to the external surface of the heart to affect a decrease in the volume of the left ventricle. Other disclosed devices include catheters and elastic bands that are usable in these treatments. Finally, disclosed is a device having an anchor disposed proximate the heart's apex, a plurality of petals, and a tensioning band secured to at least one of the petals.

8 Claims, 12 Drawing Sheets

U.S. PATENT DOCUMENTS

| | | |
|---|---|---|
| 5,738,626 A | 4/1998 | Jarvik |
| 5,749,839 A | 5/1998 | Kovacs |
| 5,749,855 A | 5/1998 | Reitan |
| 5,798,102 A | 8/1998 | McMichael |
| 5,800,528 A | 9/1998 | Lederman |
| 5,824,071 A | 10/1998 | Nelson |
| 5,827,220 A | 10/1998 | Runge |
| 5,843,156 A | 12/1998 | Slepian |
| 5,848,962 A | 12/1998 | Feindt |
| 5,888,241 A | 3/1999 | Jarvik |
| 5,908,378 A | 6/1999 | Kovacs |
| 5,957,916 A | 9/1999 | Jeevanandam |
| 5,957,977 A | 9/1999 | Melvin |
| 5,971,910 A | 10/1999 | Tsitlik |
| 6,007,479 A | 12/1999 | Rottenberg |
| 6,022,328 A | 2/2000 | Hailey |
| 6,045,497 A | 4/2000 | Schweich |
| 6,059,715 A | 5/2000 | Schweich |
| 6,063,115 A | 5/2000 | Gealow |
| 6,077,214 A * | 6/2000 | Mortier et al. ............ 600/16 |
| 6,077,218 A | 6/2000 | Alferness |
| 6,086,526 A | 7/2000 | Francischelli |
| 6,125,852 A | 10/2000 | Stevens |
| 6,152,144 A | 11/2000 | Lesh |
| 6,155,968 A | 12/2000 | Wilk |
| 6,155,972 A | 12/2000 | Nauertz |
| 6,165,119 A | 12/2000 | Schweich |
| 6,165,120 A | 12/2000 | Schweich |
| 6,165,121 A | 12/2000 | Alferness |
| 6,165,122 A | 12/2000 | Alferness |
| 6,174,279 B1 | 1/2001 | Girard |
| 6,193,648 B1 | 2/2001 | Krueger |
| 6,200,280 B1 | 3/2001 | Brenneman |
| 6,221,103 B1 | 4/2001 | Melvin |
| 6,234,960 B1 | 5/2001 | Aboul-Hosn |
| 6,238,334 B1 | 5/2001 | Easterbrook |
| 6,238,429 B1 | 5/2001 | Markowitz |
| 6,241,654 B1 | 6/2001 | Alferness |
| 6,264,602 B1 | 7/2001 | Mortier et al. |
| 6,293,906 B1 | 9/2001 | Vanden Hoek |
| 6,360,749 B1 | 3/2002 | Jayaraman |
| 6,375,608 B1 | 4/2002 | Alferness |
| 6,387,042 B1 | 5/2002 | Herrero |
| 6,402,679 B1 | 6/2002 | Mortier |
| 6,402,680 B2 | 6/2002 | Mortier |
| 6,409,760 B1 | 6/2002 | Melvin |
| 6,425,856 B1 * | 7/2002 | Shapland et al. ............ 600/37 |
| 6,685,620 B2 * | 2/2004 | Gifford et al. ............ 600/16 |
| 6,887,192 B1 * | 5/2005 | Whayne et al. ............ 600/16 |

FOREIGN PATENT DOCUMENTS

| | | |
|---|---|---|
| WO | WO 97/40755 | 11/1997 |
| WO | WO 99/49926 | 10/1999 |
| WO | WO 00/72909 A1 | 12/2000 |

OTHER PUBLICATIONS

Ro Winslow, Gene Therapy In Studies Show Promise, The Wall Street Journal, Nov. 14, 2001, p. B7.

* cited by examiner

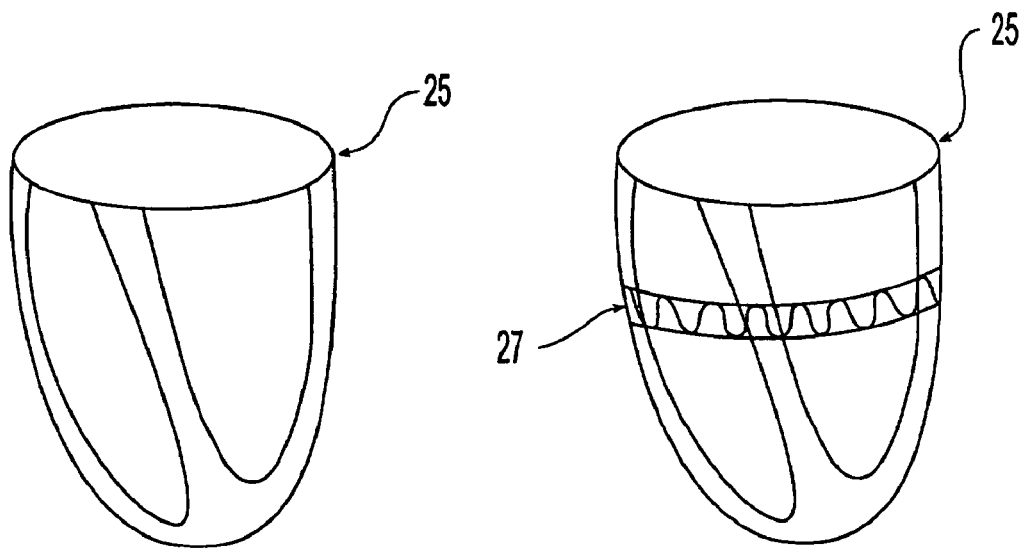
Fig. 7A
(Prior Art)
Fig. 7B
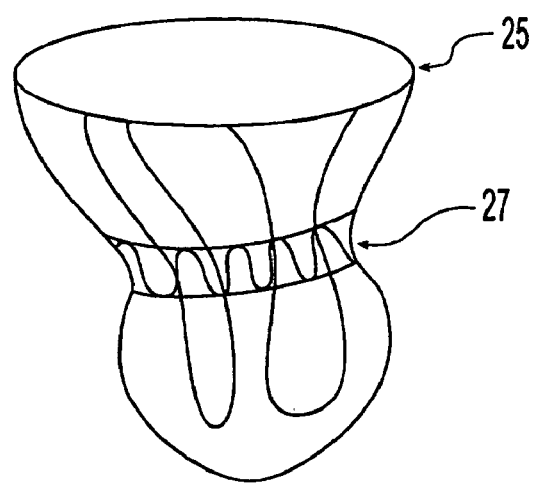
Fig. 7C

MODIFICATION OF PROPERTIES AND GEOMETRY OF HEART TISSUE TO INFLUENCE FUNCTION

CROSS-REFERENCE TO RELATED APPLICATION

This application is a continuation of U.S. application Ser. No. 09/988,293 filed Nov. 19, 2001 now U.S. Pat. No. 6,685, 627, which is a continuation-in-part of U.S. application Ser. No. 09/414,708 filed Oct. 8, 1999, now U.S. Pat. No. 6,360, 749, and claims the benefit of U.S. Provisional application No. 60/103,824 filed Oct. 9, 1998, the contents of which are expressly incorporated herein by reference thereto.

FIELD OF THE INVENTION

This invention relates to treatment of heart failure and more particularly, treatment of heart failure by reducing the internal volume of a dilated and diseased left ventricle.

BACKGROUND OF THE INVENTION

Congestive heart failure is a chronic, degenerative condition that impairs the heart's ability to pump blood at normal filling pressures to adequately meet the energy requirements of the body. It is estimated that 4.9 million Americans suffer from various degrees of congestive heart failure (CHF), with about 400,000 new cases identified each year. Heart failure is the most common diagnosis in hospital patients over the age of 65, and it carries a mortality rate higher than that for malignant tumors. One in five CHF patients dies within one year of diagnosis and only 15% survive more than 10 years.

There is no cure for CHF short of a heart transplant. However, advances in pharmacology have provided improved treatment programs. Multidrug treatment regimens that include diuretics, vasodilators and inotropic agents such as angiotensin-converting enzyme (ACE) inhibitors, can slow the progression of CHF and reduce the number of acute episodes. However, treatment remains directed at symptoms and is most effective in the early stages of CHF.

In later stages of the disease, mechanical devices can play an important role. Speciality left ventricular pacemakers can improve the heart's function as a pump, while cardiac assist devices may be used to help support the failing heart. These devices primarily address the needs of approximately 25% of CHF patients.

The increase in CHF has inspired researchers to look for new ways to treat this disease, leading to the development of drugs, surgical procedures and mechanical pumps to assist heart function, which either prevent or at least delay progression of the condition. One such approach involves implantation of an artificial heart, comprising, a diaphragm pump, an example of which is described in U.S. Pat. No. 4,468,177. The pump disclosed in this patent comprises two chambers which are driven in a "push-pull" manner so that the volumes of each of the two chambers are alternatively enlarged and reduced and, further, both chambers are in the path of fluid through the pump. However the use of this, or a similar, pump arrangement for total heart replacement or heart assistance would require an extremely reliable, durable and portable power supply. Although mechanical pumps have been constructed and tested, they have not been found to be adequate for long-term treatment of heart failure.

Chronic heart failure is characterized by changes in the biochemical composition of the ventricular wall, the orientation of cardiac muscle fibers, and the geometry of the ventricular chamber. Remodeling is the term commonly used to describe these facets of cardiac adaptation in disease. While some aspects of the remodeling process may be beneficial to overall heart function to this disease, other aspects are likely to be maladaptive over extended periods. One notable maladaptive aspect of remodeling is left ventricular dilatation, which is characterized not only by an increase in ventricular end diastolic volume but also by shifts of the end diastolic pressure volume relation toward larger volumes. Ventricular dilation increases wall stress and imparts mechanical disadvantage to the myofibrils; therefore, it is a critical event in the disease process.

A decrease in the internal volume of the damaged left ventricle will increase its efficiency because the amount of oxygen consumed by the myocardial muscle as it pumps is related to the wall tension developed during ventricular contraction. The wall tension, in turn, is proportional to the fourth power of the diameter of the ventricular cavity. Therefore, at a given smaller diameter, less work will be used by the muscle to pump a given volume of blood against a given pressure.

Cardiac output has been improved surgically by reducing the volume of a diseased left ventricle. Removal of the non-functioning aneurysmatic segment of the heart muscle has improved the hemodynamic situation by changing the geometry of the left ventricle, leading to enhanced cardiac output. However, this procedure, generally referred to as the Batista technique, is associated with considerable operative risk.

An improvement upon this operation is disclosed in U.S. Pat. No. 5,738,626. In this modified surgical procedure, which includes elements of the other approaches as well, the dilated left ventricle is first reduced in size via myocardial resection and then the heart is supported and assisted by the attachment of a cardiomyoplasty muscle wrap. Cardiomyoplasty is a term used to describe a procedure in which the sheetlike latissimus dorsi muscle is mobilized (while maintaining its vascular supply) and inserted into the mediastinum through a lateral thoracotomy. After pericardiectomy, the muscle is wrapped around both the left and right ventricles. Several weeks are provided for surgical recovery and electrical muscle conditioning, and thereafter the muscle is paced by burst stimulation synchronized to every other cardiac systole. Chronic repetitive stimulation induces biochemical and physiological transformations in the muscle, altering its characteristics toward those of cardiac muscle. These changes include fatigue resistance, prolonged contraction duration, diminution in size, and reduced maximal power.

The principal mechanism by which cardiomyoplasty has been assumed to assist the failing heart is augmentation of systolic ejection by active squeezing of the ventricles. While human studies have reported improvement in the clinical symptoms of patients undergoing this therapy, evidence for active systolic assist has been inconsistent. The results have led some to speculate that more passive external constraining effects of the muscle wrap maybe a source of benefit.

Surgical modes of intervention for the treatment of heart failure include: stiffening zones of acute infarction, for example by directly injecting glutaraldehyde into the affected tissue; wrapping a skeletal muscle (stimulated electrically) around the heart to augment ventricular contractility; and applying an epicardial marlex mesh to support the weakened and distended left ventricle.

A disadvantage common to cardiomyoplasty procedures, which is a consequence of the use of skeletal muscle as the ventricular wrap, is that the tissue wrap fatigues upon repeated stimulation at normal heart rates. Therefore, a period of time exceeding several weeks is required after this operation to condition the skeletal muscle, transforming it into a different tissue, rich in mitochondria and adapted to withstand the repeated stimulation with much less fatigue. During this period a ventricular assist pump may be implanted within a hole cut in the ventricle. Eventually, this assist pump will be removed.

Today, ventricular assist devices (VAD) designed to support a failing heart, represents the most important device technology for treating CHF. These devices are manufactured by Thermocardiosystems (TCS: Woburn, USA), Thoratec (Berkeley, USA), Abiomed (Danvers, USA), and Novacor (Santa Ana, USA).

Some heart remodeling techniques are also under development. Cardio Technologies (Pine Brook, N.J.) is developing a cardiosupport system, that acts via direct mechanical ventricular activation which mimics open chest resuscitation. The device squeezes the heart by applying pressure to a cup-like component placed around the heart.

Acorn Cardiovascular (New Brighton, Minn., USA) envisions a completely new technology for the treatment of CHF. The company is developing a passive device made of biocompatible materials that is placed around the heart via minimally invasive surgical techniques. The device is able to reduce the size, preventing the heart from enlarging further. Unlike surgical reduction techniques (Batista techniques), the product does not require the removal of any heart muscle.

Additional developments are illustrated in the following patents.

U.S. Pat. No. 5,749,855 issued to Reitan et al. describes implantable catheter pump including a drive cable, with one end of the drive cable being connectable to a drive source, a collapsible drive propeller being adjustable between a closed configuration in which the collapsible drive propeller is expanded so as to be operative as an impeller, and a sleeve extending between one side of the collapsible drive propeller and the other side of the collapsible drive propeller.

U.S. Pat. No. 5,908,378 issued to Kovacs et al. describes a cardiac assist device comprising of an outer shell and a diaphragm, formed of polyurethane copolymer.

U.S. Pat. No. 5,824,071 describes an apparatus for treatment of ischemic heart disease by providing transvenous myocardial perfusion.

U.S. Pat. No. 5,798,102 describes a method of treating cardiomyoplasty with a composition comprising beta-amyloid, streptolysin O and growth hormone.

U.S. Pat. No. 5,702,343 describes a cardiac reinforcement device and method of treatment of cardiomyopathy. This device provides for reinforcement of the walls of the heart by constraining cardiac expansion, beyond a predetermined limit, during diastolic expansion of the heart. This device is applied to the external wall of the heart and surrounds the complete cardiac wall.

U.S. Pat. No. 5,738,626 discloses a cardiomyoplasty procedure comprising excision of the tissue of the myocardium and replacing it with a muscle wrap. This muscle is conditioned with a support device.

U.S. Pat. No. 5,848,962 issued to Feindt et al. describes a half shell which is placed against the ventricle and an external filling unit which compresses the shell synchronously with cardiac activity, enhancing the ejection fraction of the ventricle.

U.S. Pat. No. 5,800,528 describes a passive girdle which is wrapped around a heart muscle which constrains the dilatation during diastole. The girdle is formed of a material and structure that does not expand away from the heart but may, over an extended period of time be decreased in size as dilatation decreases.

U.S. Pat. No. 5,282,849 issued to Kolff et al. describes a ventricle assist device with volume displacement chamber.

U.S. Pat. No. 4,902,291 issued to Kolff et al. describes a collapsible artificial ventricle and pumping shell.

Nevertheless, none of the above approaches is wholly satisfactory for the treatment of congestive heart failure. Therefore, there is a need for additional or alternative methods for treatment heart pump failure.

SUMMARY OF THE INVENTION

This present invention relates to devices, materials and methods and is directed toward treatment of heart failure by physically modifying the diseased or damaged heart tissue in such a manner that the internal volume of the damaged left ventricle is reduced, thereby improving the pumping efficiency of the diseased heart and ameliorating the symptoms of heart failure.

One embodiment of this invention comprises a catheter-based, minimally invasive procedure that will introduce biocompatible materials into the left ventricle of the heart. Part of the left ventricular cavity will be filled with biocompatible material which will be applied and attached to the left ventricle using catheter-guided techniques and equipment rather than conventional cardiosurgical procedures. The biocompatible filling materials introduced will decrease the volume of the left ventricle and improve the hemodynamics of the heart, thereby alleviating the symptoms of heart failure.

A second embodiment, which may be used either alone or in combination with the first embodiment, comprises direct injection of suitable, substantially non-compressible biocompatible materials into the wall of the left ventricle. This procedure will increase the bulk of the wall and thereby diminish the interior volume of the left ventricle. These materials may also strengthen and reinforce the wall as well, diminishing the risk that the ventricle might rupture.

The biocompatible filler materials to be used in both embodiments of this invention will exist in a substantially liquid state while they are delivered to the heart. They will then be converted to a second, substantially rigid state when they are attached to or injected within the wall of the left ventricle. Also contemplated in this invention are filler materials which will expand to a predetermined volume as they undergo the transition from the first, substantially liquid state to the second, substantially rigid state. These could also be foam-like materials which increase or decrease in size depending on the desired mechanism of action. The filler materials may include at least one of genetically modified therapeutic agents and growth factors, for example, genetically-engineered muscle cells and muscle fibers.

A third embodiment of the method relates to a method for treating heart failure comprising attaching at least one band to the surface of a human heart comprising a left atrium, a right atrium, a left ventricle and a right ventricle, thereby compressing the heart, whereby cardiac performance is improved. The internal volume of at least one of the left atrium, right atrium, left ventricle, and right ventricle can be decreased by this method, preferably by attaching a plurality of elastic bands to the surface of the heart. If desired, cross-links between a plurality of circular elastic bands attached to the surface of the heart can be provided. If desired, the circular elastic bands can be substantially horizontally positioned and substantially parallel to one another, wherein the bands are of varying diameter arranged in order of descending size from the atria toward the ventricles in order to form a conical structure on the outer surface of the heart.

The at least one attached band may preferably be made of wire and be adjustable in diameter, and wherein the diameter is adjusted according to monitored action of the heart. If desired, the at least one band can include other monitoring or diagnosis features, such as means for conductance of electrical signals to and from cardiac tissue, or means for delivery of drugs to the heart. The drugs may include at least one of genetically modified therapeutic agents and growth factors, for example, genetically-engineered muscle cells and muscle fibers. The at least one band can be attached to the surface of the heart by an attaching means selected from the group consisting of sutures, clamps, bio-compatible adhesives, or combinations thereof. The method can be used to decrease the internal volume of any one or all of the left atrium, right atrium, left ventricle, and right ventricle.

The invention also relates to a device for the treatment of congestive heart failure, in the form of a band configured and dimensioned to apply force to the outer surface of a human heart and made of at least one biocompatible elastic component selected from the group consisting of metallic materials, synthetic elastomeric materials, rubber materials, biological materials, stent graft materials and combinations thereof. Advantageously, additional features can be built into the biocompatible elastic components. For example, at least one of the biocompatible components can be electrically conductive. Preferably, the device is constructed in the form of a stent, optionally covered with a biocompatible elastomeric synthetic material such as muscle or other biological tissue. Also, the device may be constructed in the form of a cup-shaped stent, which stent is adjustable in size.

Other embodiments of this device include a band which is adjustable in diameter, which is introduced in a compact state and is released in vivo for placement around at least the left ventricle of the heart. The device can include elastic bands which are stretched before placement around the heart, and which include cross-links therebetween, wherein the elastic bands are substantially horizontally positioned and substantially parallel to one another, are of varying diameter arranged in order of descending size from the atria toward the ventricles, whereby a conical structure is formed on the outer surface of the heart. The band may alternatively be made of a resilient synthetic biocompatible material which overcomes flexing movements of heart muscles and which does not fracture upon long term flexing.

The present invention also is related to an apparatus for application around a heart with an apex. The apparatus includes a first portion having an anchor that is configured and dimensioned to be disposed proximate the apex, and a second portion having a plurality of petals and a retaining region, with the petals being resiliently biased. The anchor is retained in the retaining region and at least one of the petals is biased to provide compressive force against at least a portion of the heart.

In some embodiments, a tensioning band is included and is secured to at least one of the petals. The tensioning band may permit selective tightening of at least one of the petals. Also, two or more of the first portion, the second portion, and the tensioning band may be integrally formed. A screw mechanism may be provided for increasing or decreasing the compressive force applied by at least one of the petals. The first portion may be disposed about at least a portion of a ventricle. The anchor may be retained in the retaining region at least in part by a male-female interlock, and the petals may extend from the second portion proximate the retaining region. The petals may be uniformly spaced with respect to each other.

BRIEF DESCRIPTION OF THE DRAWINGS

FIGS. 7A, 7B and 7C depict the shape of a dilated heart in normal diastole (FIG. 7A), and when provided with a band, the shape of that dilated heart during systole (FIG. 7B) and diastole (FIG. 7C).

DETAILED DESCRIPTION OF THE INVENTION

Figure 1:
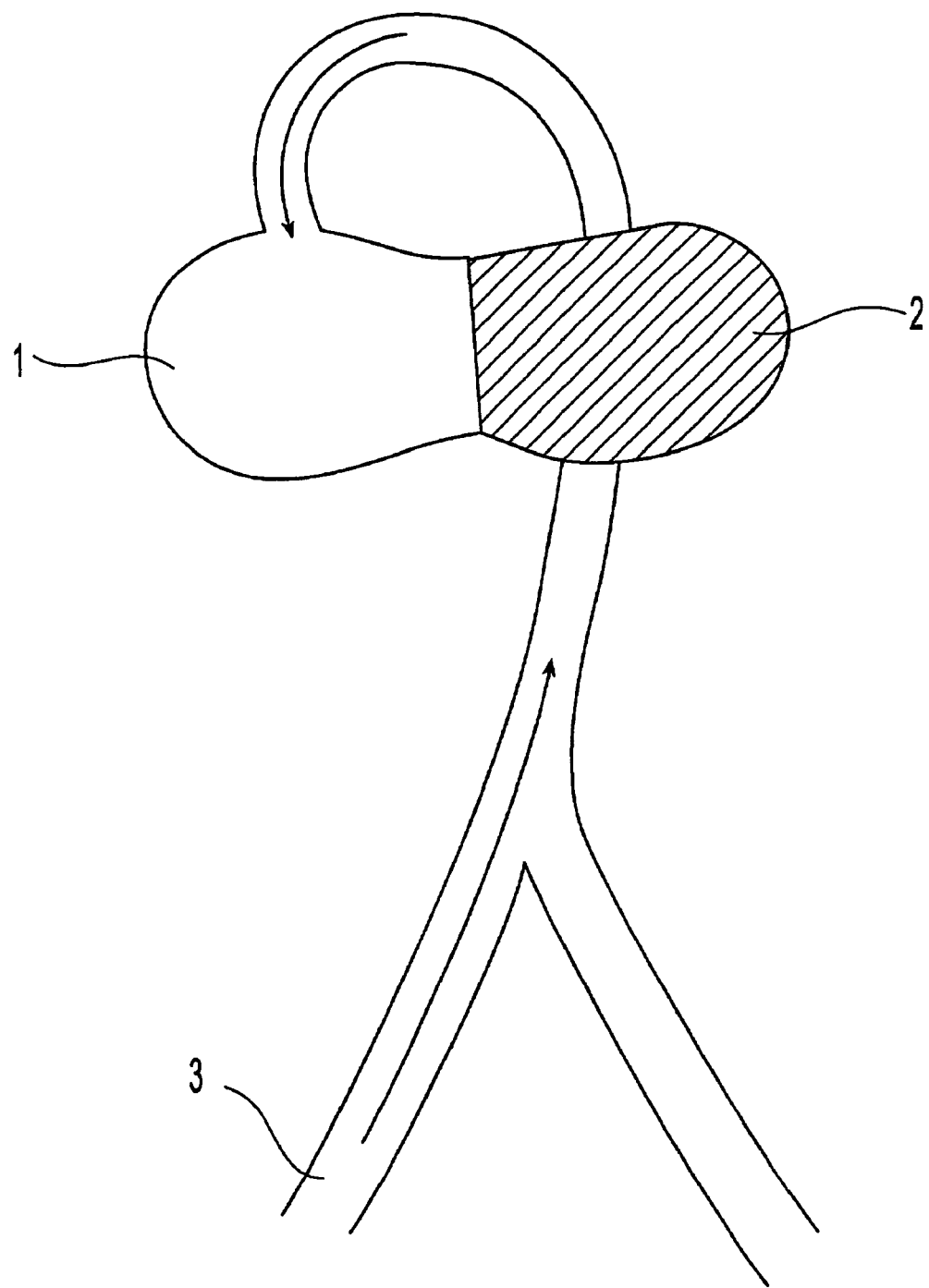
FIG. 1 is a schematic representation of a diseased left ventricle of a heart depicting the left ventricular aneurysm (2) present in the diseased portion of the left ventricle. This figure also displays peripheral vascular access to the damaged site (3) and the non-diseased section of the left ventricle (1).

This invention describes approaches to be taken for the treatment of heart failure which avoid resection of diseased heart muscle. Various novel treatment methods, materials and devices are disclosed.

In one embodiment of this method, part of the diseased, expanded left ventricle will be partially filled with biocompatible materials which either will be attached to the wall directly or to a stabilizing skeleton attached to the wall. This will modify the geometry of the heart due to the introduction of the biocompatible material to decrease the internal volume of the left ventricle and thereby improve its geometry and hemodynamics. In a second embodiment, which may be used independently or in conjunction with the first embodiment, appropriate, biocompatible materials may be injected directly into the diseased tissue thereby thickening, reinforcing and strengthening or revitalizing the cardiac wall and, simultaneously, decreasing the internal volume of the left ventricle, thereby increasing cardiac efficiency. In a third embodiment of the method, at least one elastic band is placed around the outer surface of a human heart to compress one or more of the left atrium, right atrium, left ventricle and right ventricle to improve cardiac performance.

Damaged regions of the left ventricular cardiac wall may be defined and mapped by procedures well known in the art including both computer imaging and ventricular wall motion analyzers. Once this has been done, either or both embodiments of this invention may be utilized to treat heart failure resulting from the damage to the wall of the left ventricle.

The first embodiment of this invention comprises the use of a catheter for the introduction of biocompatible materials into the left ventricle. These materials may be coated upon or within a supporting skeleton within the heart. This embodiment also encompasses the delivery of filler materials into a container that may either be attached directly to the cardiac wall within the left ventricle or it may be attached to a stabilizing skeleton that will be fixed to the wall of the ventricle.

This embodiment also encompasses application of suitable biocompatible materials directly to the surface of the wall of the left ventricle. These filler materials may be used to increase the bulk of that part of the cardiac wall, decreasing the volume of the left ventricle. These materials may also be used to induce the retraction of the wall to which they are attached. Here the filler materials on the wall would shrink, condense or retract as a result of a physical or chemical change, causing a corresponding retraction of the wall of the ventricle. In addition, the state or phase of the material can be converted as it is introduced into the heart to cause expansion of the material and reduction of the volume of the heart. The filler materials may include at least one of genetically modified therapeutic agents and growth factors, for example, genetically-engineered muscle cells and muscle fibers.

Another embodiment of this invention comprises direct injection of biocompatible materials into the diseased tissue of the left ventricle to revitalize it or to increase its bulk and, consequently, improve the properties of the wall and to decrease the internal volume of the left ventricle. Suitable materials for this purpose would include, but not be limited to, angiogenic agents, collagen, fibrinogen, foams or hydrogels which are well known in the art. More generally, this invention contemplates the use of the group of substances referred to in the art as "polymeric endoluminal paving system" materials as biocompatible filler materials. Heart failure could be treated with such injections, either alone or in conjunction with the decrease in the volume of the left ventricle that would be obtained through the first embodiment of this invention.

These embodiments of this invention will generally employ a steerable application catheter which will be introduced into the left ventricle either by direct percutaneous access or by transluminal vascular access by retrograde passage of the aortic valve. The application catheter will be capable of being reversibly attached to the cardiac wall. Attachment of the steerable application catheter to the wall of the ventricle will allow the precise and accurate delivery of biocompatible filler materials, stabilizing skeletons, cutting means and tissue removal means to predetermined locations within the heart.

Furthermore, the application catheter will transport a stabilizing skeleton attached to the catheter by a reversible release mechanism. The application catheter may carry the stabilizing skeleton either internally or externally. The release mechanism, deploying the stabilizing skeleton, will be reversible to allow the retrieval of the stabilizing skeleton.

The application catheter may also be attached by a first reversible attachment means to a stabilizing skeleton which, in turn has a second reversible attachment means by which it may be attached to the wall of the ventricle. The catheter is attached only indirectly to the wall of the ventricle through the stabilizing skeleton. Furthermore, in this instance, the delivery means for the biocompatible filler material would be located at a point on the stabilizing skeleton proximal to the second attachment means and distal to the junction between the catheter and the stabilizing skeleton defined by the first attachment means.

The first attachment means may be any joining member or procedure which reversibly connects the catheter to the skeleton. The second attachment means can be any attachment member, such as an anchoring, screw or other fastener for fixing the stabilizing skeleton to the wall of the left ventricle at one or more points. The stabilizing skeleton may comprise arrangements of flexible filaments or elastic wires comprising suitable, biocompatible materials. The stabilizing skeleton may also comprise a network or mesh of such filaments and, if desired, a flexible, expandable container.

The application catheter of this invention may also have cutting and retrieval elements. These will allow removal of part of the cardiac wall as needed, for example, for attachment of the application catheter, attachment of the stabilizing skeleton, application of suitable materials to the surface of the cardiac muscle, and injection of the filler material into the wall. The cutting and retrieval elements of the application catheter may also be used to remove the filler material from the heart, prior to the extraction of the support skeleton if that were to become desirable or necessary.

The application catheter of this invention will also comprise means by which the biocompatible filler material will be coated upon or inserted within the wall of the ventricle. These means can include any tube or conduit which can direct the filler material to the heart. In addition, filler material distribution elements can be used to direct the filler material to the proper location. In this embodiment, the elements can be used to directly apply substantially liquid filler material upon the surface of the ventricular wall. The catheter may also carry suitable means to initiate the physical and chemical changes that would be necessary to allow the biocompatible filler material to adhere to the surface of the wall. Alternatively, the catheter can include components for the injection of biocompatible filler material directly into the wall. These components are preferably needles or include needle-like tubular elements for injection of materials, which elements are advantageously positioned substantially perpendicular to the site of injection. The injection component may also be composed of a plurality of needles or needle-like elements placed at the proximal end of the catheter and oriented at an angle to the longitudinal axis of the catheter to allow a wider area of the wall of the ventricle to be treated at one time. Preferably, this angle would be between 20 and 60 degrees and is preferably about 30 degrees. Also contemplated are needle means in the form of elongated tubular members projecting radially from the application catheter. Here the catheter may be placed within the heart wall, using for example a void or pit constructed with the cutting and retrieval elements described above. The filler material would then be injected in a direction substantially perpendicular to the long axis of the catheter and substantially parallel to the surface of the cardiac wall. This embodiment of the invention contemplates multiple, retractable needles allowing a radial dispersion of the biocompatible filler material within the cardiac muscle.

The biocompatible filler materials generally are in a fluid, substantially liquid state before they are introduced into the ventricle. Once in place these materials undergo a phase transition into a substantially non-compressible form, essentially rigid state, as they are attached to or injected within the wall of the ventricle. The biocompatible filler may also be a material that is both compressible and expandable. In this instance, the filler material would first be compressed while it is delivered to the heart and then allowed to expand to a pre-determined volume within the heart. The filler material will be extruded from the application catheter onto a supporting skeleton which supports a flexible, expandable container. The filler will be firmly attached to or confined within the supporting skeleton in order to avoid embolization caused by the flow of the blood stream and the dynamics of the heart.

The expandable, flexible container contemplated by this invention may be attached directly to the cardiac wall or to a stabilizing skeleton or support that is fixed to the wall. In this approach, the filler material or materials will be injected into the skeleton or container until it expands to a pre-determined final volume. Once filled, the container will then be sealed. Materials which can be used to fill the container would include not only the biocompatible materials applied directly to or injected within the wall of the ventricle but they could also include, for example, colloidal suspensions, contrast mixtures and conventional pharmaceutical solutions such as saline.

Expansion of the biocompatible filler may be driven by any one of a number of mechanisms. The filler material may expand upon release as a result of its inherent mechanical properties. One type material is a foam material that increases its volume upon deployment. Typical foam materials include polyurethane foams such as IVALON™ or hydrogel plugs as these materials are well known biocompatible fillers that are used in other medical applications. Another would be a spring or flexible mechanical structure based on a memory material such as nitinol wire. The expansion could also be the result of an interaction between the filler material and blood or between the filler material and the tissue surface. The expansion may also be the result of the temperature and/or pressure differences between those within the heart compared to the comparable conditions found in the catheter or other delivery apparatus.

This invention also contemplates the expansion or phase transition of filler material by the injection of liquids into a fluid-tight, sealable compartment containing the filler material. Suitable liquids, again, include colloids, saline solutions, contrast mixtures, or mixtures thereof.

It is also contemplated that a substantially non-compressible substantially rigid filler material is generated through a chemical reaction in situ in the compartment. Reagents and catalysts, if appropriate, could be provided through independent lumina of a multi-channel catheter. The reagents would be mixed and allowed to react within a sealable, fluid tight, flexible container held within the stabilizing skeleton attached to the wall of the left ventricle. The product of this reaction would have a pre-determined volume and a shape that could be constrained by a container, a stabilizing skeleton, or an expandable container held within the stabilizing skeleton. For example, reversible hydrogels may be constituted using self-assembling artificial proteins. Such protein solutions, adjusted to a first pH level could be used to fill and expand a fluid-tight container held by the support skeleton within the diseased left ventricle. Subsequent adjustment to a second pH would then induce a reversible transition of the protein solution to a substantially non-compressible, substantially rigid gel. Suitable hydrogels, with properties that would present specific advantages for application in this invention could be designed and produced by recombinant DNA methods known in the art. (Petka et al., "Reversible Hydrogels form Self-Assembling Artificial Proteins, (1998) Science 281 (Jul. 17, 1998), 389-392).

This invention further contemplates biocompatible filler materials which could be expanded to a pre-determined volume by the application of an external influence. Examples would include the expansion of suitable biocompatible fillers mediated by exposure to ultraviolet, ionizing or other radiation of an appropriate wavelength.

Still further, this invention contemplates direct attachment of the biocompatible filler material to the wall of the left ventricle. Contraction, shrinkage or compaction of a layer of filler material directly attached to the wall of the ventricle would result in a parallel contraction of that wall, thereby decreasing the internal volume of the left ventricle. Contraction of the filler material directly attached to the wall could occur over a period of time as a consequence of the nature of that material within the cardiac environment. Contraction might also occur only after a certain time period and could be mediated by the application of external factors. Such factors might include exposure to radiation of a suitable wavelength and intensity, electricity or other physical influences, injection of other interacting materials, and application of a localized source of heat or suction applied to the biocompatible filler attached to the wall of the left ventricle.

The stabilizing skeleton may be made up of biocompatible, flexible mesh-like materials, flexible filaments or from an arrangement of biocompatible elastic wires. As noted above, the stabilizing skeleton generally includes means for reversible attachment to both the application catheter and the cardiac wall. It will also be capable of collapsing into a compact structure that may transported, either upon or within the attachment catheter, to, or from, the site of its attachment within the body. Once set in place within the body the stabilizing skeleton will be expanded to the shape and size with which it will be used for the attachment of filler materials. The stabilizing skeleton may also contain within it, or have attached to it, an expandable container into which filler material can be injected.

The stabilizing skeleton may also be used for the mechanical support of a predetermined section of the wall of the left ventricle. This structure could be applied to the internal surface of the left ventricle prior to the injection of biocompatible filler materials within the wall.

In another embodiment, the biocompatible filler may be added by injection directly through the diseased heart wall. A variety of suitable syringes are useful for this purpose, with the biocompatible material carried by the syringe body and then injected through the needle into the heart. One of ordinary skill in the art can select an appropriately sized needle to deliver the selected biocompatible material via this pericardial access.

In addition, the biocompatible material can be, or include, a genetic material that operates on the heart tissue over time to enhance its mass or performance. Typical genetic materials include angiogenic factor or growth factor, and these are preferably added with a biocompatible material so that the biocompatible material initially reduces the volume of the heart followed by the action of the genetic material on the heart wall over time. For example, genetically-engineered muscle cells and muscle fibers can be introduced along with one or more filler materials. Genetically-modified cells and growth factors suitable for injection according to the present invention include those described, for example, in "Gene Therapy in Heart Studies Shows Promise," The Wall Street Journal, Nov. 14, 2001, p. B7, the content of which is incorporated herein by reference. These genetically-engineered cells and fibers, referred to as muscle growth factors, facilitate the growth of new cells and capillaries in the myocardium. Therefore, in this instance, not only is the volume of the ventricle reduced, but perfusion of the myocardium is also increased as well. Therefore, biocompatible filler materials may be selected from the group consisting of a self-expanding foam, a hydrogel, gelatin, collagen, fibrinogen, elastin, water-absorbing microspheres, muscle growth factors, and combinations thereof.

The amount of biocompatible material filler to be introduced is that which will reduce heart volume to levels that control the diastolic ("D") and systolic ("S") levels to desired ranges. Typically, the heart ejection function ("F") can be calculated by the following equation:

$$F=[(D-S)/D]\times 100\%$$

Values of 60 to 75% and particularly 65% are desired. Thus the optimum volume of biocompatible material to be introduced into the heart is that which can increase the F value to 65%. Example 1 illustrates how this is done.

An additional method for reduction of the volume of the ventricle, which can be used either alone or in combination with the other procedures and compositions of the present invention, is designated Ventricular Geometry Reduction. In this method an elastic strap or band is attached to the external surface of the heart and thereby compresses the heart in such a manner as to decrease the effective internal volume of one or more cardiac chambers. Consequently, cardiac systolic and diastolic cycles are performed with substantially decreased blood volumes, thereby increasing the efficiency of the pumping action of the CHF-afflicted heart.

In one embodiment of this procedure, one or more bands formed from a metal or a combination of metal and a synthetic material, are attached to the external wall of the ventricle. This band, or these bands, may be sutured onto the ventricular wall such that the ventricular wall is pulled closer together thus reducing the volume of the ventricle. That is, since the left ventricle is dilated considerably in CHF, the walls of the ventricle may be pulled together whereby an overlap of the wall tissue is formed and held in this physically constricted state, thus causing a significant reduction in the volume of the ventricle. This decrease in the effective volume of the left ventricle decreases the contractile force required to expel blood from that ventricle.

In another embodiment of this procedure, one or more bands may be attached to the outer wall of the heart to reduce the radius of the ventricle. These bands may comprise a set of bands of decreasing diameters, which can be attached to the exterior surface of the heart, and which may be crosslinked to one another to form a conical structure surrounding and supporting the heart, whereby the radius of the ventricle is reduced.

Bands can be placed through minimally invasive surgery, using, as a non-limiting example, fluoroscopy procedures to guide their positioning and placement. In addition, other imaging techniques, including the use of a Noga catheter for example, can be used to monitor ventricular function, and to identify and map those regions of the wall that are functioning poorly or not at all. Evaluation of the mapping information obtained is used to guide placement of the band or bands on the wall of the heart. Similar imaging procedures can be used after application of the bands of the present invention, to verify an improvement in cardiac function.

In further embodiments of this procedure, the bands attached to the heart are capable of transmitting an applied electrical impulse to stimulate contraction of the heart. Here, the band may be temporarily, or permanently, connected to electrical leads, which could be used to pace the heart by either increasing or decreasing the frequency of contraction. Similarly, in another embodiment, the cardiac bands are constructed to allow the delivery of one or more drugs to the heart in a programmable manner. Drug delivery can be provided as a continuous infusion or through intermittent doses. In both instances, the timing and rate of delivery of the drug can be regulated by means of an external, programmable interface. These applications are in contrast to muscle wraps, which have been used to support the heart, that have, essentially, failed because the muscle fibers by themselves have no contracting motion and, therefore, simply lie over nonfunctioning or only poorly-functioning cardiac tissue.

Once one or more bands are attached to the heart, cardiac improvement methods, including, but not limited to transmyocardial revascularization or percutaneous myocardial revascularization may be carried out using laser, ultrasound, or RF ablation or other, appropriate, mechanical processes.

The bands may be attached to one or more regions of the heart. For example a band may be positioned so that it surrounds the ventricle in such a manner that it reduces both the systole and diastole. In this instance, the band exerts a constrictive force on the ventricle and thereby remodels the geometry of the heart, and improves the functioning of the heart. In one example, the band or bands may be placed around the ventricles in order to improve the injection fraction of the heart. When appropriate, the band or bands may be placed only around the left ventricle. Here the band can be one formed in the shape of an arc, similar to, but more elastic than, conventional annuluplasty rings that are placed around the mitral valve. In this instance, the diameter of the semicircular band encompasses the left ventricle, while the arms of the arc are placed around the ventricular chamber, and adhered thereto by suitable means. In another embodiment of the present invention, both the systole and diastole of a failing heart can also be improved by attaching one or more bands around the entire heart in such a manner that both the atria and the ventricles are enveloped.

The bands may be constructed as stents which may be formed of any of a number of suitable, biocompatible materials. For example, the bands may be constructed of one or more metals, or appropriate synthetic materials, and may have one or more openings within the band. These bands can also be made from stent graft material, which may be applied to either the inside or the outside of the stent or on both sides of the stent. The band, formed as a stent, may be manufactured employing processes comprising one or more of laser cutting, chemical etching, photomachining techniques, and metal injection molding.

The bands can also be constructed as adjustable rings, which may comprise a metallic component, that can be placed over the top of the left ventricle only. Such an adjustable ring, which has been positioned over the top of the left ventricle, may be clipped or sutured onto that ventricle, or otherwise attached using materials and procedures know to those in the art. The bands may also be shaped as a cusp having one or more stent-like elements with an adjustable diameter.

The band may also comprise a cover of a synthetic material and it may be formed between two layers of synthetic material, which may conduct electricity. The bands may also be covered with a biological material, including, but not limited to, muscle tissue or elastic tissue, which may be capable of conducting electricity. Where the band is coated with muscle tissue, the band can have three functions: volume reduction of the left ventricle, an electrical function and stimulation of the electrical function of the heart. In one embodiment of the present invention, electrical stimulation can be used to control movement of one or more bands attached to the heart, in such a manner as to mimic normal heart function.

The bands are preferably designed to be contractible or collapsible to a compact configuration to facilitate introduction into the patient. A small incision can be made with the compact band inserted within an introducing catheter in a manner similar to that used for introducing stents into the vascular system. The bands are then deployed and expanded or otherwise allowed to change into their final configuration and location in place around the outer surface of the heart.

The methods and means by which this invention leads to a reduction in heart volume may be understood more clearly by reference to FIGS. 1 to 16. As represented in FIG. 1, heart failure may be the result of an aneurism (2) that has formed in the wall of the left ventricle (1) of the heart. The expanded ventricle functions inefficiently not only because of the presence of damaged, poorly functioning cardiac tissue unable to pump effectively, but also because of the increase in the volume of the left ventricle resulting from dilatation of the cardiac wall within the aneurism. The ensuing cardiomyopathy is life-threatening and a successful medical intervention necessitates an improvement in the ability of the heart to contract effectively. Non-surgical access to the damaged regions, both for diagnosis and treatment, may be obtained through the peripheral vascular system (3).

Figure 2:
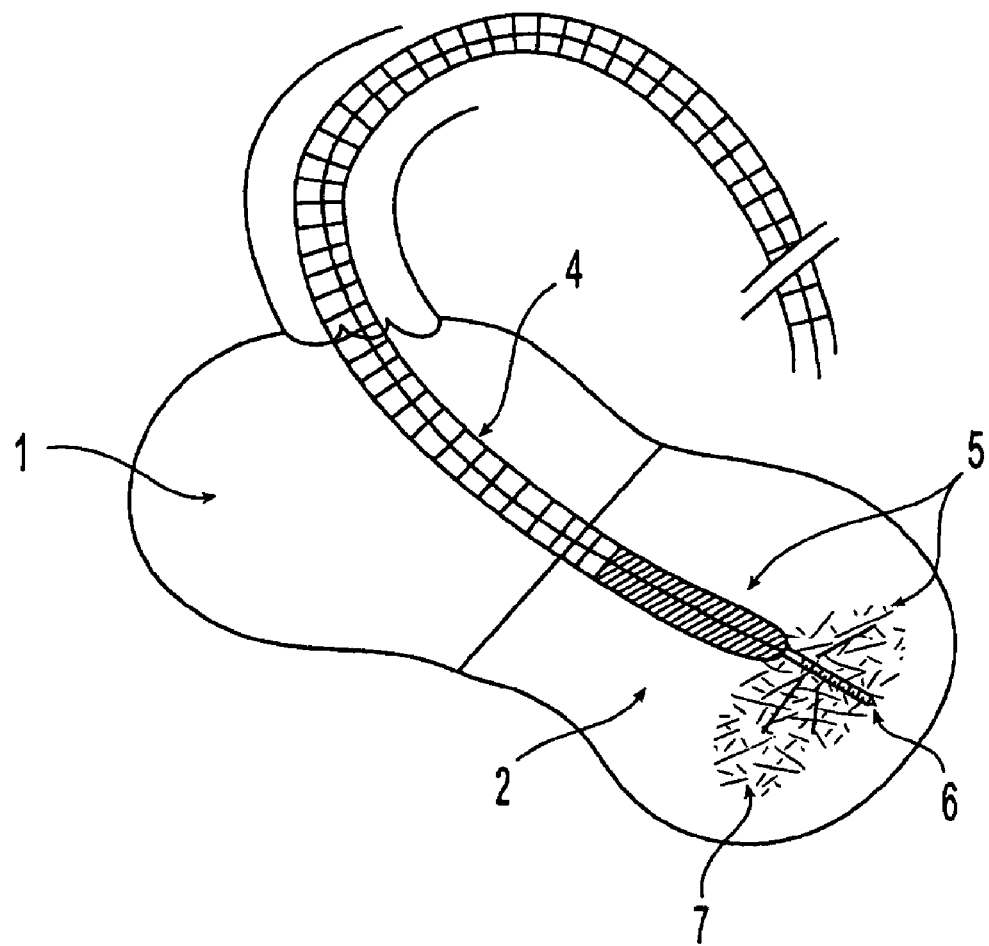
FIG. 2 depicts the catheter to be used for the application of filling materials into the left ventricular cavity, the filling material expanding after release from the catheter, the screw-like fixture holding the catheter in place and the expanded stabilizing skeleton.

In one embodiment of this invention, depicted in FIG. 2, a catheter (4) is passed through the peripheral vascular system into the left ventricle (1). Once in position, the catheter is attached to the cardiac wall using a screw-type reversible attachment member (6). A suitable biocompatible filler material (5) is then extruded through the catheter and into the left ventricle where it will expand, solidify and adhere to a stabilizing skeleton (7) which would have been previously deployed within the left ventricle, and may, in fact, be attached to the cardiac wall through reversible attachment means.

Figure 3:
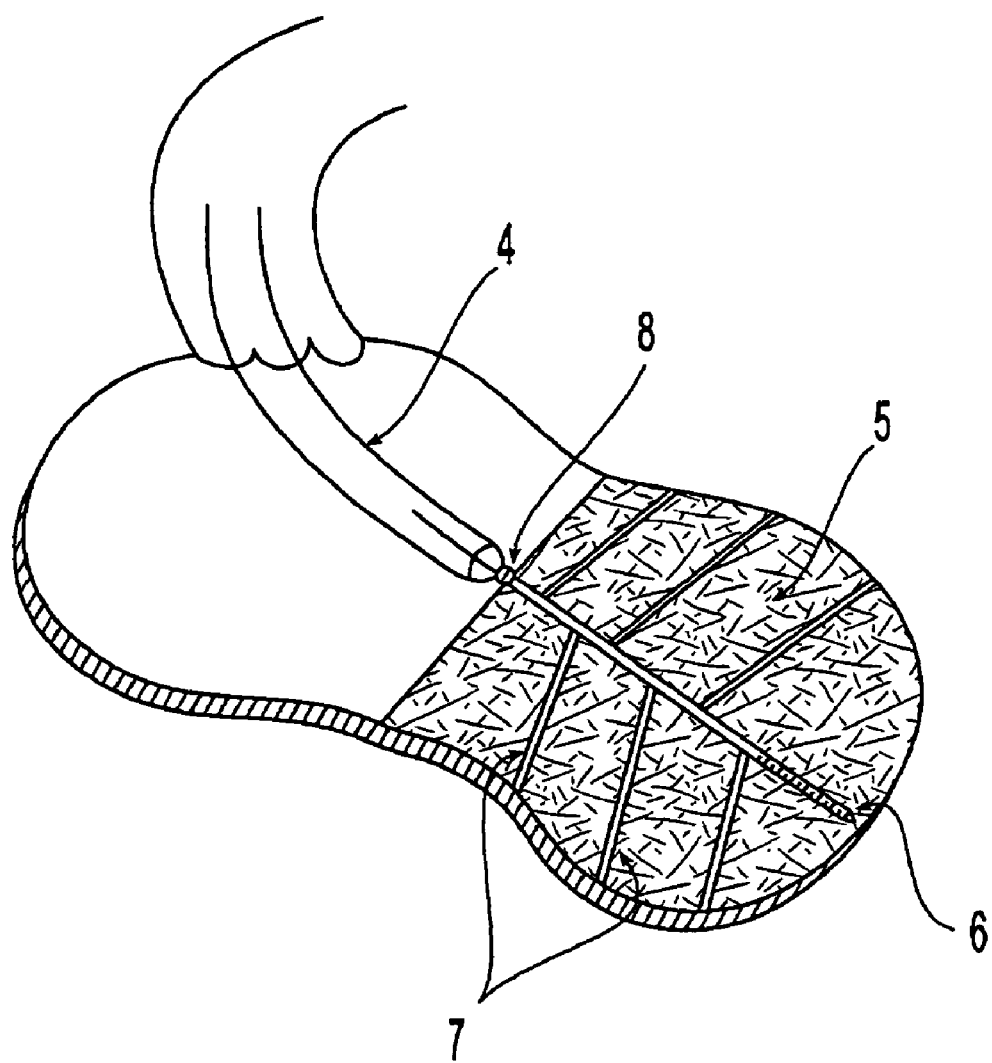
FIG. 3 reveals the release mechanism and the presence of the filling material in the left ventricle as the application catheter is withdrawn.

FIG. 3 depicts the solidified filler material (5), attached to the stabilizing skeleton (7). This figure also reveals another reversible attachment means (8), in the form of an anchor, such as a hook, needle clamp or the like, for connecting the catheter (4) with the stabilizing skeleton (7). Once the filler material, attached to the stabilizing skeleton, is in place, the catheter (4) is detached from the stabilizing skeleton (7), by means of the reversible connection (8) between the catheter and the stabilizing skeleton, and withdrawn from the heart.

Figure 4:
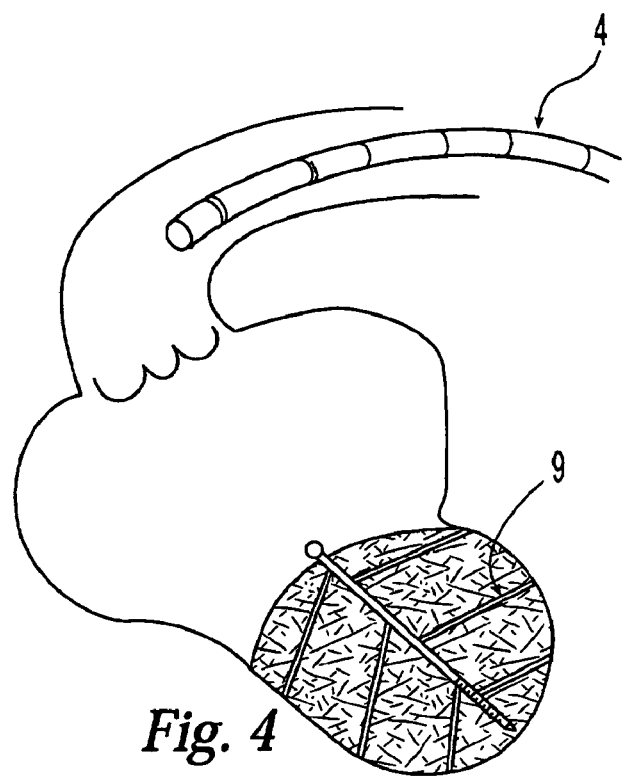
FIG. 4 shows the filling material placed within the stabilizing structure attached to the wall of the left ventricle with the application catheter being removed.
Figure 5:
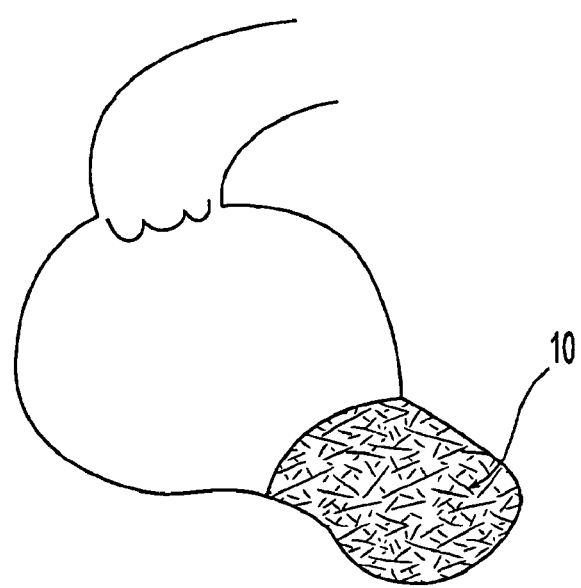
FIG. 5 depicts filling material which contracts while still attached to the wall of the left ventricle, thereby decreasing the internal volume of the left ventricle.

FIG. 4 depicts the removal of the catheter (4) from the heart, with the biocompatible filler material attached to the stabilizing skeleton (9). The expanded filler material (10), in place within the left ventricle, will thereby decrease the internal volume of the heart and improve the pumping efficiency of the left ventricle. FIG. 5 depicts an embodiment in which the biocompatible filler material has contracted after it had been put in place, drawing the attached cardiac wall, thereby further decreasing the internal volume of the heart.

Figure 6A:
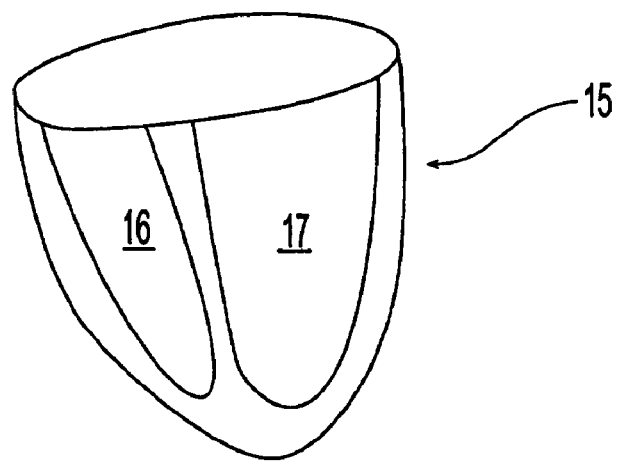
FIGS. 6A and 6B are representations of the cardiac ventricular wall, showing the right and left ventricles before (FIG. 6A) and after (FIG. 6B) placement of an elastic band of the invention around the ventricle.
Figure 6B:
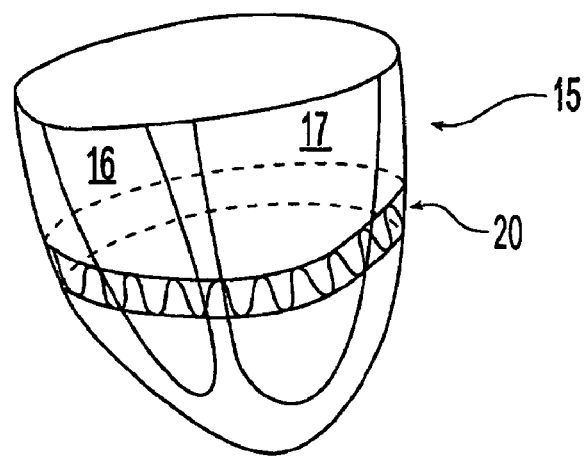

FIG. 6 is a representation of the cardiac ventricular wall of a heart (15), showing the right (16) and left (17) ventricles. FIG. 6B illustrates the heart after placement of a band (20) around the ventricle. As shown, the band (20) tightens to compress the heart, thus reducing its volume. This volume reduction enables the heart to pump more efficiently.

FIG. 7 depicts the shape of a dilated heart (25) in normal diastole (FIG. 7A). The shape of that dilated heart when provided with a band (27) during systole is shown in FIG. 7B and during diastole is shown in FIG. 7C. During systole, when the ventricle contracts, the band squeezes the volume of the heart, thereby increasing its ejection fraction.

Figure 8A:
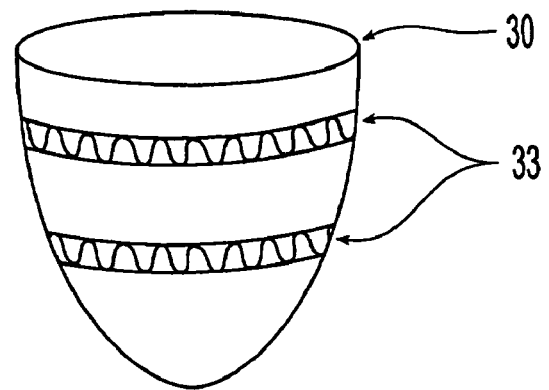
FIGS. 8A and 8B depict a heart wrapped with a plurality of bands, either with (FIG. 8A), or without (FIG. 8B) interconnections between the bands.
Figure 8B:
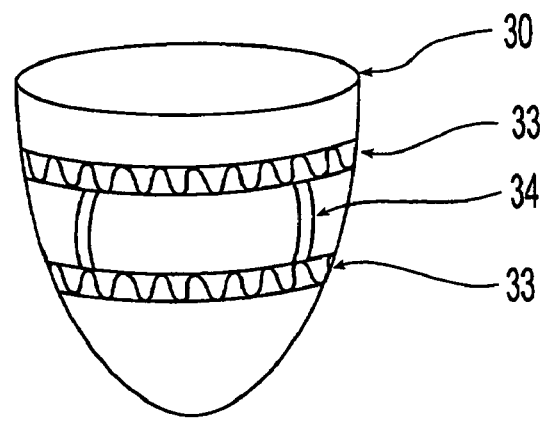

FIGS. 8A and 8B depict another embodiment wherein the heart (30) is wrapped with a plurality of parallel bands (33). FIG. 8A illustrates non-interconnecting bands which are useful for applying pressure in different locations, whereas FIG. 8B illustrates parallel bands which have interconnections (34) therebetween for increased strength and for applying more localized pressure.

Figure 9:
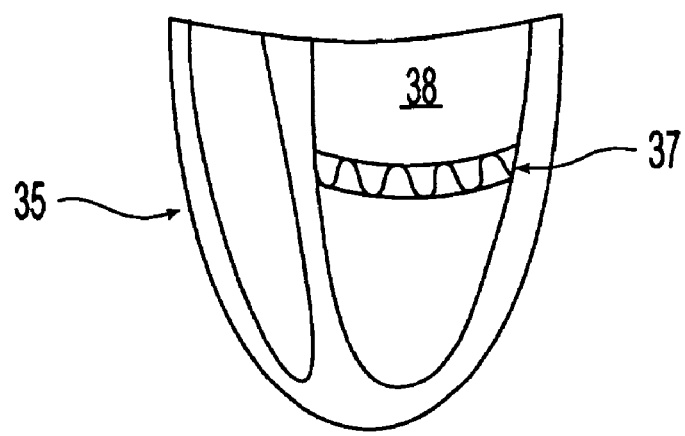
FIG. 9 shows a heart with a band placed only around the left ventricle.
Figure 10:
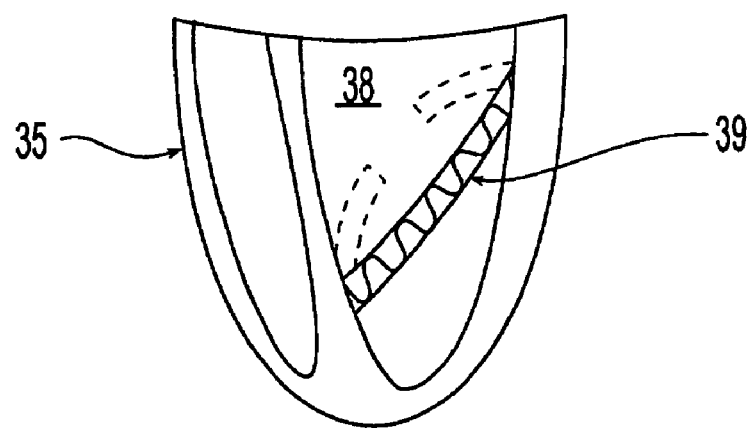
FIG. 10 illustrates a heart with a semi-circular band placed around the left ventricle.

FIG. 9 represents a heart (35) with a band (37) placed only on the left ventricle (38). This illustrates that the volume of that ventricle alone can be reduced. FIG. 10 illustrates a semi-circular band (39) that is used for the same purpose. One of ordinary skill in the art will realize that this technique could be used to selectively reduce the volume of any one particular heart chamber or any combination of heart chambers, depending upon the extent of the heart disease.

Figure 11:
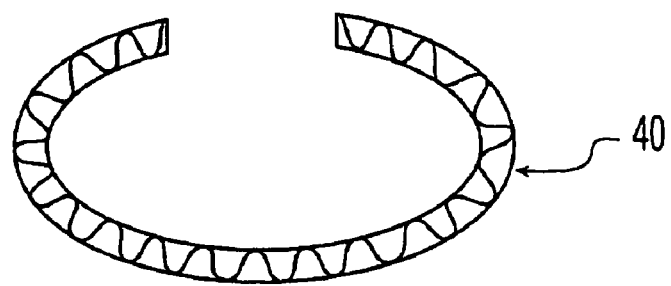
FIG. 11 is a top view of a semi-circular elastic band which is to be placed around the left ventricle.
Figure 12:
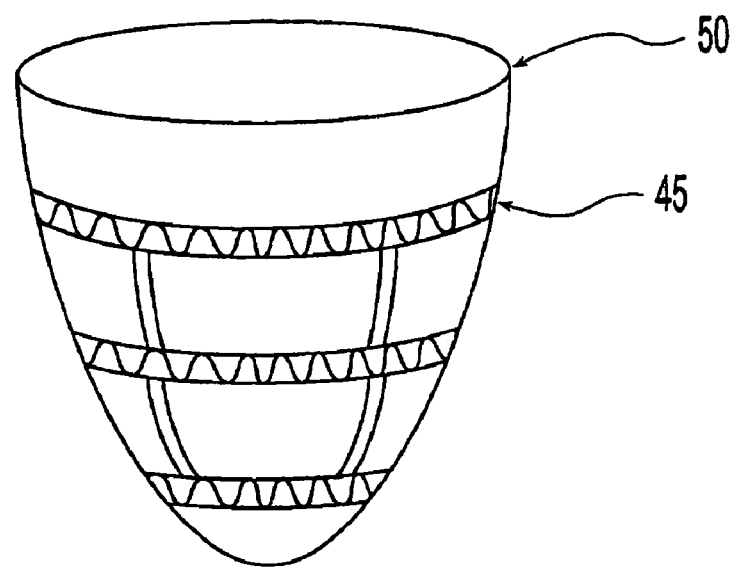
FIG. 12 shows a heart provided with a plurality of interconnected bands of decreasing diameter, which form a conical structure therearound.

FIG. 11 depicts a view of semi-circular band (40) to be placed primarily around the left ventricle of the heart. FIG. 12 illustrates that a plurality of interconnected bands (45) of decreasing diameter can be used to form a conical restriction shape on that part of the heart (50). If desired, the bands can be configured into a conical shape which completely surrounds around the heart.

Figure 13:
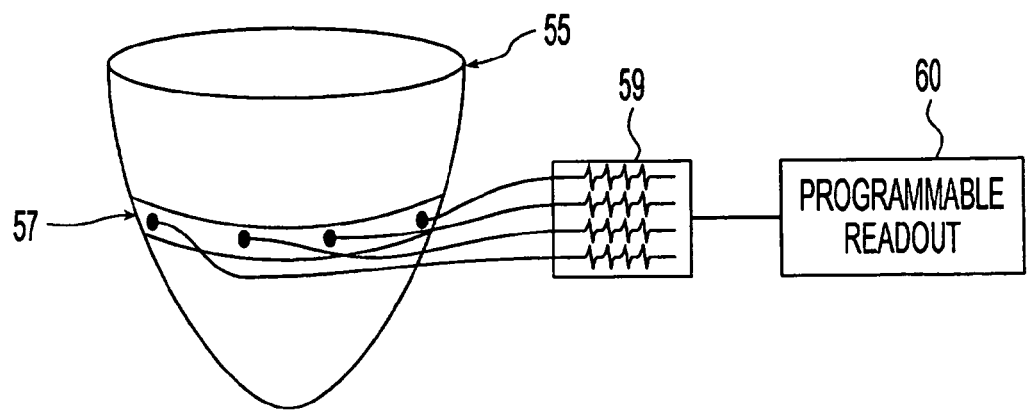
FIG. 13 illustrates a heart wrapped with a band comprising electrical leads whereby the expansion and contraction of the heart may be monitored and whereby contraction may be electrically stimulated.

FIG. 13 depicts a heart (55) wrapped with a band (57) comprising electrical leads (58) whereby the expansion and contraction of the heart may be monitored (59) and whereby a contraction may be electrically stimulated. Advantageously, the monitoring of the electrical signals can be displayed on a programmable read out device (60).

Figure 14:
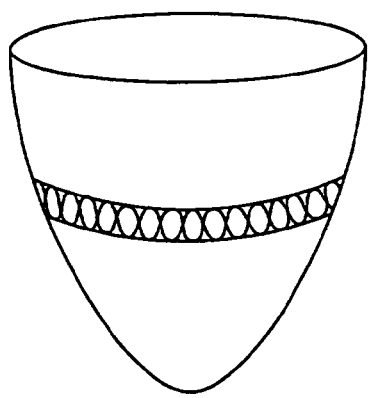
FIG. 14 illustrates a heart wrapped with a band comprising one or more conductive polymers which modulate the function of the tissues surrounding the heart.

FIG. 14 illustrates a heart wrapped with a band comprising one or more conductive polymers which can modulate the function of the tissues surrounding the heart. Other heart assisting features can be built into these bands, such as the delivery of drugs, dyes, or other materials to assist in enhancing or monitoring the performance of the heart.

In some prior art embodiments, a jacket or cusp is placed around the heart or the left ventricle. This has the potential to compress some of the arteries that supply blood to the heart muscle.

Figure 15:
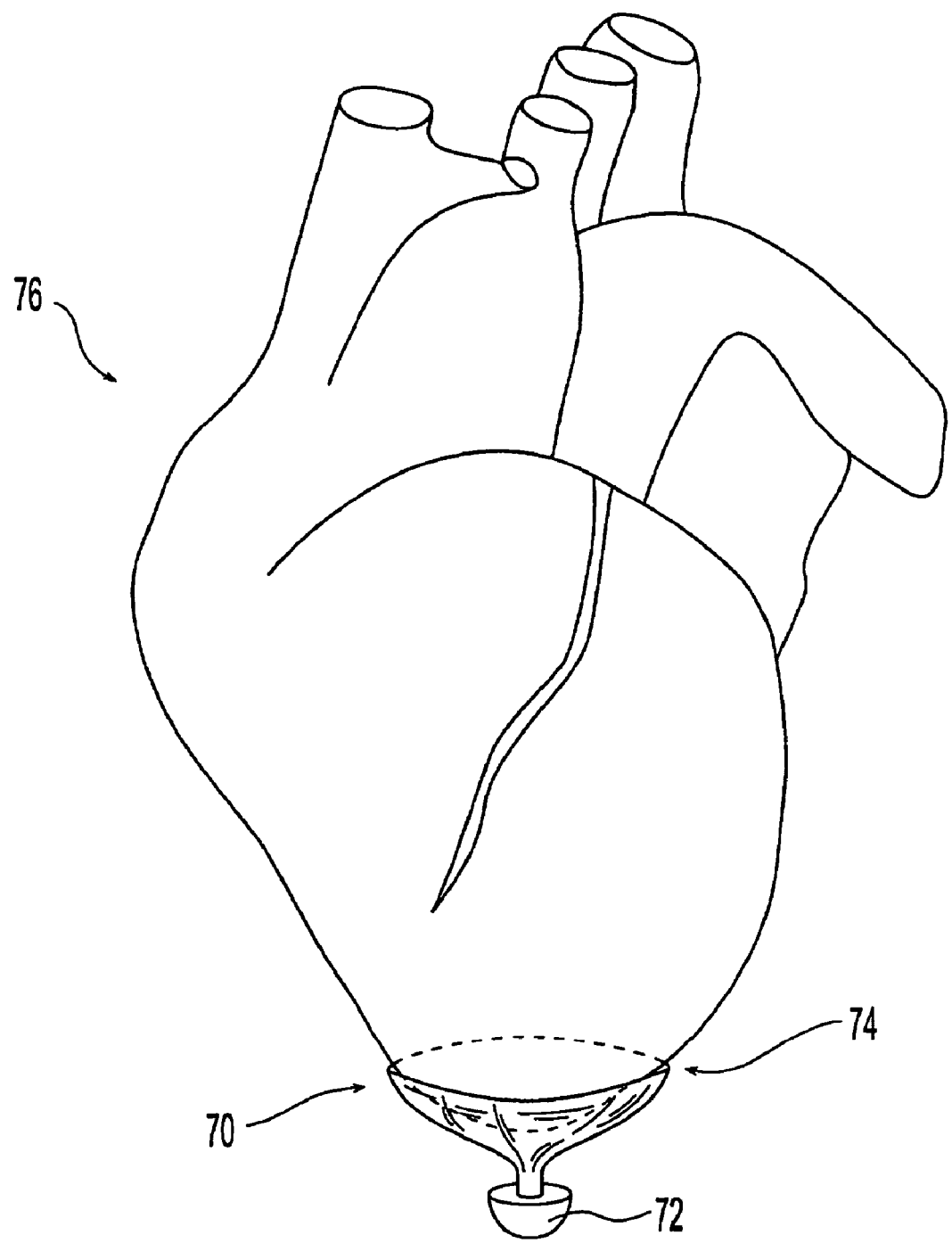
FIG. 15 illustrates a jacket, provided with a cusp like anchor, for attachment to the apex of a heart.

As shown in FIG. 15, an apparatus for application around a heart with an apex may include a jacket (70) provided with a cusp like anchor (72). The jacket (70) may be attached to the apex (74) of a heart (76), for example using sutures, to elevate apex (74) and thereby reduce the volume of heart (76) at apex (74).

Figure 16:
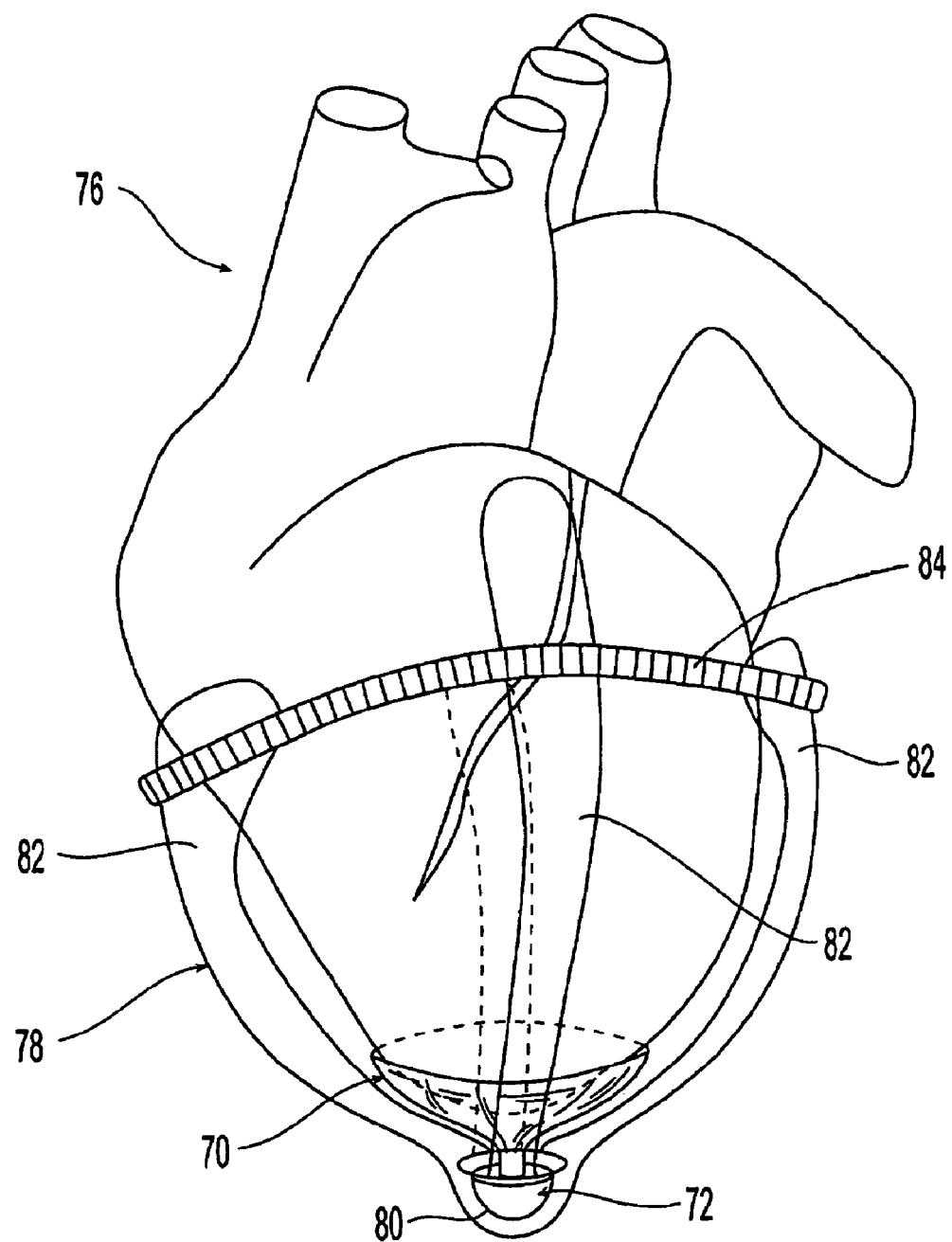
FIG. 16 illustrates a petal-like structure for coupling to the jacket of FIG. 15.

As shown in FIG. 16, a petal-like structure (78) may be coupled to jacket (70), with anchor (72) of jacket (70) interlocking with a suitably shaped retaining region (80) so that anchor (72) is securely retained therein. Anchor (72), for example, may be secured in retaining region (80) by a male-female interlock. Each petal (82) of structure (78) may extend from region (80), proximate apex (74). Any suitable mechanism, such as a screw mechanism, may be provided for loosening or tightening petals (82) about heart (76).

In one embodiment, as many as twelve petals (82) are provided about the periphery of heart (76) with its various chambers. The petals may be uniformly spaced, or alternatively spaced in non-uniform fashion about the periphery. In one exemplary embodiment, petals (82) are formed from a metal or polymer. Petals (82) may be clip-like, and may be resiliently biased to apply a compressive force around at least a portion of heart (76), for example, to decrease the volume of a ventricle. In some exemplary embodiments, a tensioning band (84) may be secured to one or more of petals (82) to permit selective tightening using a tightening force remote from retaining region (80) and apex (74). The petals (82) connected by tensioning band (84) may be adjacent one another, or more remotely located from one another. In general, the structure of tensioning band (84) is like or comparable to the structure of the bands previously described, and accordingly is not repeated. Further, biocompatible materials introduced into the heart, as previously described, may be used in combination with jacket (70), petal-like structure (78), and tensioning band (84) to effect the desired volume reduction in at least a portion of the heart. In some exemplary embodiments, tensioning band (84), for example, may be attached to multiple petals (82), and provided with means to permit petals (82) to be selectively tightened or loosened so that a desired compressive force is applied to heart (76).

In some embodiments, jacket (70), petal-like structure (78), and tensioning band (84) are provided as separate components, while in other embodiments two or more of jacket (70), petal-like structure (78), and tensioning band (84) may be integrally provided.

EXAMPLES

The following examples illustrate the most preferred features of the invention.

Example 1

An angiogram is used to determine the heart rate of a subject, and it is found that D=180, S=100, and F is 44.4%. Computer modeling of the heart is used to image the heart and determine where dead or non-functioning tissue is located.

A biocompatible filler material of a hydrogel is placed in the heart in the area of the non-functioning tissue. After the material is placed, another angiogram is taken to find that D=170, S=100 and F is 42%. The preceding steps are repeated until F is increased into the range of 60 to 75% and preferably, as close to 65% as possible. The final values of D=150, S=60 and F=60% are acceptable and the procedure is terminated.

Example 2

A left ventricular angiogram was done with a LV catheter and the ejection fraction was determined using the dye outflow technique. Later, a Noga catheter was used to map the ventricular wall motion to determine the areas of the ventricular wall where the tissues are ischemic.

A biocompatible filler material was introduced in the areas of the ventricular wall where the tissues were found to be ischemic. The ventricular wall mapping was repeated to notice any changes in wall motion. The wall mapping was repeated after 4 weeks, one month and six months to monitor any changes.

Example 3

The experiment of Example 3 was repeated after a filling material consisting of a biological material and a filler material was introduced inside the ventricular wall.

Example 4

After LV angiogram and LV wall mapping techniques, a filler material that contained a genetic material which enhances angiogenesis was injected into the ventricular wall. Following this, an elastic band was placed around the ventricle and the angiogram and mapping was repeated.

Example 5

After the steps described in Example 4 were completed a second band was placed parallel to the first band and around the ventricle.

For all examples, the methods described therein resulted in improved heart pumping efficiency.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An apparatus for application around a heart with an apex, comprising:
    a first portion having an anchor that is configured and dimensioned to be disposed proximate the apex;
    a second portion having a plurality of petals and a retaining region, the petals being resiliently biased; and
    a third portion having a tensioning band secured to at least one of the petals,
    wherein the anchor is retained in the retaining region and at least one of the petals is biased to provide compressive force against at least a portion of the heart.

2. The apparatus of claim 1, wherein two or more of the first portion, the second portion, and the tensioning band are integrally formed.

3. The apparatus of claim 1, wherein the first portion is adapted to be disposed about at least a portion of a ventricle.

4. The apparatus of claim 1, wherein the petals extend from the second portion proximate the retaining region.

5. The apparatus of claim 1, wherein the petals are uniformly spaced with respect to each other.

6. An apparatus for application around a heart with an apex, comprising:
    a first portion having an anchor that is configured and dimensioned to be disposed proximate the apex;
    a second portion having a plurality of petals and a retaining region, the petals being resiliently biased; and
    a third portion having a tensioning band secured to at least one of the petals,
    wherein the anchor is retained in the retaining region at least one of the petals is biased to provide compressive force against at least a portion of the heart, and the tensioning band permits selective tightening of at least one of the petals.

7. An apparatus for application around a heart with an apex, comprising:
    a first portion having an anchor that is configured and dimensioned to be disposed proximate the apex;
    a second portion having a plurality of petals and a retaining region, the petals being resiliently biased; and
    a screw mechanism for increasing or decreasing the compressive force applied by at least one of the petals,
    wherein the anchor is retained in the retaining region and at least one of the petals is biased to provide compressive force against at least a portion of the heart.

8. An apparatus for application around a heart with an apex, comprising:
- a first portion having an anchor that is configured and dimensioned to be disposed proximate the apex; and
- a second portion having a plurality of petals and a retaining region, the petals being resiliently biased, wherein the anchor is retained in the retaining region at least in part by a male-female interlock and at least one of the petals is biased to provide compressive force against at least a portion of the heart.

* * * * *